United States Patent [19]
Anolick et al.

[11] Patent Number: 5,478,905
[45] Date of Patent: Dec. 26, 1995

[54] AMORPHOUS TETRAFLUOROETHYLENE/ HEXAFLUOROPROPYLENE COPOLYMERS

[75] Inventors: Colin Anolick, Wilmington; Viacheslav A. Petrov, Wilmington; Bruce E. Smart, Wilmington; Charles W. Stewart, Newark; Robert C. Wheland, Wilmington, all of Del.

[73] Assignee: E. I. Du Pont de Nemours and Company, Wilmington, Del.

[21] Appl. No.: 384,068

[22] Filed: Feb. 6, 1995

[51] Int. Cl.⁶ .................................................. C08F 14/18
[52] U.S. Cl. .......................... 526/254; 526/204; 526/217
[58] Field of Search .................................. 526/254, 204, 526/217

[56] References Cited

U.S. PATENT DOCUMENTS

| | | | |
|---|---|---|---|
| 2,963,468 | 12/1960 | Cleaver | 526/254 |
| 3,051,677 | 8/1962 | Rexford | 526/254 |
| 3,062,793 | 11/1962 | Eleuterio | 526/254 |
| 3,287,339 | 11/1966 | Sianesi et al. | 526/254 |
| 4,001,351 | 1/1977 | Roura | 526/254 |
| 4,105,716 | 8/1978 | Sakai et al. | 526/254 |
| 4,696,989 | 9/1987 | Oka et al. | 526/254 |

FOREIGN PATENT DOCUMENTS

| | | | |
|---|---|---|---|
| 0150953 | 8/1985 | European Pat. Off. | 526/254 |
| 1348354 | 10/1987 | U.S.S.R. | C08L 23/02 |

OTHER PUBLICATIONS

Ser. No. 08/384041 filed Feb. 6, 1995.

*Primary Examiner*—Joseph L. Schofer
*Assistant Examiner*—N. Sarofin

[57] ABSTRACT

Disclosed herein are novel amorphous tetrafluoroethylene/hexafluoropropylene (TFE/HFP) copolymers, which are more random than previous amorphous TFE/HFP copolymers, as well as a novel high productivity continuous process for making these polymers. The polymers are particularly useful in the form of coatings, films and encapsulants.

12 Claims, 1 Drawing Sheet

FIG. 1

AMORPHOUS TETRAFLUOROETHYLENE/HEXAFLUOROPROPYLENE COPOLYMERS

FIELD OF THE INVENTION

This invention concerns tetrafluoroethylene/hexafluoropropylene copolymers which are amorphous. They may be produced by a novel high pressure continuous process.

TECHNICAL BACKGROUND

Amorphous perfluorinated polymers are highly useful, particularly as coatings and encapsulants, because of their unusual surface properties, low refractive index, low dielectric constant, etc., and the relative ease of coating or encapsulating objects with such polymers. However, the use of such polymers has been limited because of their high cost, which usually derives from the high cost of the monomers and/or the high cost of the polymerization process to make the polymers. Therefore, such polymers, and the processes for making them, which are lower in cost are constantly being sought.

U.S. Pat. No. 3,062,793 describes amorphous copolymers of tetrafluoroethylene (TFE) and hexafluoropropylene (HFP) which are made by a high pressure free radical polymerization. The only process described therein is a batch process which has a relatively low productivity.

SUMMARY OF THE INVENTION

This invention concerns a continuous polymerization process, comprising, contacting at a pressure of about 41 MPa to about 690 MPa, and a temperature of about 200° C. to about 350° C., tetrafluoroethylene, hexafluoropropylene, and a radical initiator, to produce an amorphous polymer which contains at least 30 mole percent of repeat units derived from said hexafluoropropylene, at least 1 mole percent of repeat units derived from said tetrafluoroethylene, and provided that said continuous polymerization has an average residence time of about 1 second to about 60 minutes.

This invention also concerns an amorphous polymer, consisting essentially of repeat units of the formula:

(a) at least about 30 mole percent of $$-CF_2-CF(CF_3)- \qquad (I)$$

(b) at least about 1 mole percent $$-CF_2-CF_2- \qquad (II)$$

and (c) 0 to about 10 mole percent $$-CF_2-CFX- \quad \text{or} \quad -CF-CF- \qquad (III)$$
$$\phantom{-CF_2-CFX- \quad \text{or} \quad -CF} \diagdown \diagup$$
$$\phantom{-CF_2-CFX- \quad \text{or} \quad -CF-} (CF_2)_m$$

wherein X is $-C_nF_{2n+1}$ or $-OC_nF_{2n+1}$, m is 2, 3 or 4, and n is an integer of 2 to 20; and provided that in said polymer less than 20 mole percent of (I) is present in the form of triads.

DETAILS OF THE INVENTION

The TFE/HFP copolymer made herein is amorphous. By an amorphous polymer is meant that the polymer has a heat of melting of less than 5 J/g when measured by Differential Scanning Calorimetry (DSC) at a heating rate of 10° C./min. This is measured on a "first heat", that is virgin polymer is heated to at least 300° C. in the DSC (at 10° C./min), and the heat of melting, if any, is measured.

These polymers are made via a continuous polymerization process in which the initial ingredients are fed to the reactor in an essentially continuous manner and in which the product stream is essentially continuously withdrawn at approximately the same rate at which the ingredients are added. Such types of reactions are generally known to the artisan, see for instance H. F. Mark, et al., Ed., Kirk-Othmer Encyclopedia of Chemical Technology, 3rd Ed., vol. 19, John Wiley & Sons, New York, 1982, p. 880–914. Such continuous reactors include continuous stirred tank reactors and pipeline (tubular) reactors. Under the conditions employed in the process as described herein, the productivity of the process is exceptionally high. By productivity herein is meant the weight of polymer produced in a unit volume of reactor in a unit volume of time. Productivities herein are reported as kg/L/hr.

The process described herein has typical productivities of about 0.8 to about 6 kg/L/hr. By contrast, a batch polymerization, making a somewhat similar polymer, reported in U.S. Pat. No. 3,062,793, has productivities (from the Examples) of about 0.01 to about 0.03 kg/L/hr, more than an order of magnitude less than that for the continuous process. This means a lower cost for polymer produced by the continuous process.

The process is run at a pressure of about 41 to about 690 MPa (~6,000 to ~100,000 psi), preferably about 55 to about 172 MPa (~8,000 to ~25,000 psi), more preferably about 62 to about 152 MPa (~9,000 to about 22,000 psi), and especially preferably about 69 to about 103 MPa (~10,000 to ~15,000 psi). As pressure drops towards 41 MPa the molecular weight of the polymers formed and the conversion of monomers to polymer both tend to drop.

It is preferred that solvents not be used in the process, since at these pressures the monomers, particularly HFP, usually dissolve the polymer. Nonetheless, solvents can be used in the reactor. If the final product is to be a polymer solution, making the polymer solution directly may be preferable, to reduce costs (see Example 43). Sometimes for convenience in handling, small quantities of initiator are best introduced when diluted to a larger volume with a small amount of solvent (see Example 51). Solvent may also be used for other reasons, such as to help keep lines clear of polymer, particularly at lower pressures. When solvents are used it is preferred that they be essentially inert under process conditions. Useful solvents include perfluorodimethylcyclobutane and perfluoro(n-butyltetrahydrofuran).

The polymer is soluble in the monomer(s) under the process conditions. Therefore, one method of polymer isolation is to reduce the pressure below that required for solution of the polymer, and isolate the polymer from that, as by decantation, filtration or centrifugation. Indeed, it may not be necessary to reduce the pressure of the unreacted monomers to atmospheric pressure, but merely that required for phase separation of the polymer. Therefore these monomers can be recycled with only a "partial" repressurization, thereby saving energy costs. Alternatively the pressure can be reduced to atmospheric pressure, while the volatile monomers are vented off, leaving the product polymer. The monomers can of course be recovered and reused.

The apparatus for running the polymerization may be any suitable pressure apparatus in which the reactant and product streams may be added and removed at appropriate rates. Thus the apparatus may be a stirred or unstirred autoclave, a pipeline type reactor, or other suitable apparatus. Agitation is not necessary, but preferable, especially to obtain polymers with low MWD's. The material of construction should be suitable for the process ingredients, and metals such as stainless steel are often suitable.

The polymerization is carried out (reactor wall temperatures were actually measured) at about 200° C. to about 350° C., preferably about 225° C. to about 325° C., more preferably about 250° C. to about 300° C. The initiator is chosen so that it will generate active free radicals at the temperature at which the polymerization is carried out. Such free radical sources are known to the artisan, see for instance J. Brandrup, et al., Ed., Polymer Handbook, 3rd Ed., John Wiley & Sons, New York, 1989, p. II/1 to II/65.

Suitable free radical initiators include $NF_3$, $R_fNF_2$, $R_{f2}NF$, $R_fN=NR_f$, $R_fOOR_f$, $R_fNF_2$, 5 or 6 member ring perfluorinated heterocycle containing at least one N—F group and optional $R_f$ groups, perfluoropyrrolidine, perfluorooxazoline, perfluoropiperidine, perfluoromorpholine or perfluoropiperazine, wherein $R_f$ is perfluoroalkyl, containing 1 to 20 carbon atoms and having optional in-chain oxygen. Preferred initiators are $NF_3$, $R_{f2}NF$, $R_fNF_2$, perfluoropiperazine and hindered perfluorocarbons. $NF_3$ is an especially preferred initiator. If higher molecular weight polymers are desired, the initiator should preferably not have any groups present in its structure that cause any substantial chain transfer or termination during the polymerization. Such groups usually include, for instance, organic bromides or iodides.

The amount of free radical initiator used will vary depending on process conditions. Generally speaking an effective amount is used, an effective amount being that which causes more polymerization to take place with the initiator than without. It is likely that any polymerization without deliberately added initiator present is due to adventitious impurities which can act as initiators at the high polymerization temperatures. Effort should be made to minimize these impurities, such as oxygen. A useful range of initiator concentration has been found to be about 0.003 to about 0.5 g of initiator/kg monomer, preferably about 0.1 to about 0.3 g/kg monomer. Higher or lower amounts are also useful depending on the initiator, process equipment, and process conditions used, and can readily be determined by experimentation. The initiator may be added to the reactor as a solution in the monomer(s).

While "solvents" may be added to the polymerization so that the polymerization is carried out in solution, it is preferred if little or no solvent is added. The polymer formed is soluble in the supercritical HFP under the process conditions. The polymer may be isolated simply by reducing the pressure below about 34 MPa (~5,000 psi), at which point the polymer becomes insoluble. The polymer may also be isolated as fibers or fibrils by direct flash spinning of the polymerization mixture. Small amounts of solvents may be used for convenience, as for a carrier for the initiator. FC-75, perfluoro (2-n-butyltetrahydrofuran), and the cyclic dimer of HFP are examples of useful solvents.

The polymer produced by the instant process is amorphous. Whether this type of a polymer would be amorphous depends on the composition (relative amounts of HFP and TFE), and the distribution of the two repeat units in the polymer. The polymer product should contain at least about 30 mole percent of (I) and at least 1 mole percent of (II), preferably at least 30 mole percent of (II), more preferably about 35 to about 50 mole percent of (I) and about 40 to about 65 mole percent of (II) when a dipolymer is made [no repeat unit (III) present]. Optionally up to about 10 mole percent of repeat unit (III) may be present. When (III) is present a preferred composition is about 35 to about 65 mole percent (I), about 35 to about 65 mole percent (II), and about 0.1 to about 10 mole percent of (III).

All or part of the tetrafluoroethylene used in these polymerizations can be replaced with an equal weight of vinylidene fluoride ($VF_2$) giving polymers ranging from a lightly modified poly(HFP/TFE) to a low Tg poly(HFP/$VF_2$). With $VF_2$ productivities have been observed up to 8.1 kg/l l/hr, 2–3X the productivity observed with HFP+TFE under comparable conditions. Other partially fluorinated or hydrocarbon monomers may also polymerize using our methods. This may include monomers such as ethylene, propylene, vinyl fluoride, trifluoroethylene, 1,1,1-trifluoropropene, 1,1,1,3,3-pentafluoropropene, and 1,1,1,2-tetrafluoropropene.

As mentioned above, the properties of the polymer will be affected not only by the overall composition of the polymer, but by the distribution of the various monomer units in the polymer. The instant process yields a polymer in which the monomer units are more uniformly distributed in the polymer, which gives a polymer with more consistent properties and better thermal stability. One measure of polymer uniformity is randomness of the monomer units in the polymer. A measure of this is relative amounts of isolated repeat units, diads, triads etc. By diads and triads are meant instances in which two or three repeat units from the same monomer, respectively, occur in the polymer.

Many of the polymers made by the process described herein have relatively small amounts of triads of repeat unit (I), which of course derived from HFP. Thus in such polymers less than 20 mole percent of (I) is in the form of triads, and preferably less than about 15% and more preferably less than about 10%. As would be expected, in polymers with higher amounts of (I), there is a tendency towards higher triad content. The amount of triads in the polymer can be determined by $^{19}F$ NMR (see below for procedure). See Examples 23 and 33–36 and Comparative Example 1 for triad amounts in various polymers.

The instant TFE/HFP copolymers are more stable thermally than prior art polymers. For example, a 58 wt % HFP/42 wt % TFE copolymer made by the instant process lost 20% of its weight when heated to 420° C. while a 57 wt % HFP/43 wt % TFE copolymer made by prior art lost 20% of its weight when heated to only 340° C. (Comparative Example 1). The lower thermal stabtility of the prior art polymer is likely the result of its higher HFP triad content, long HFP blocks being believed to be relatively unstable thermally.

The instant polymers also have a narrower molecular weight distribution (MWD) than prior art polymers. By MWD is meant the weight average molecular weight divided by the number average molecular weight (Mw/Mn). Polymers described herein often have MWD's of less than 5, preferably less than 4. Such polymers often have superior physical properties.

Repeat unit (III) may be present to help suppress crystallization and/or lower a glass transition temperature, or for other purposes, and are derived from the corresponding α-perfluoroolefin, vinylidene fluoride, perfluorocycloolefin or perfluoro(alkyl vinyl ether). Preferred monomers for unit (III) in which —$C_nF_{2n+1}$ is present are those in which —$C_nF_{2n+1}$ is perfluoro-n-alkyl. When X is —$C_nF_{2n+1}$ it is preferred if n is 1 to 14, while if X is —$OC_nF_{2n+1}$ it is preferred if n is 1 to 4, more preferably 1 or 3.

Since TFE is considerably more reactive in the polymerization than HFP, an excess of HFP is needed to achieve the desired polymer composition. Typically this also means that at the end of the polymerization, most or all of the TFE will have polymerized, but there will be (a considerable amount of) unpolymerized HFP. In a sense this is an advantage, since the HFP can act to help carry the polymer from the reactor, and no additional carrier (such as a solvent) is needed. Typically the TFE will be about 1 to 10 mole percent of the total amount of monomer being fed to the process, with the HFP and other monomer(s) (if present) being the remainder.

The average residence time is the average amount of time any of the material fed to the reactor actually spends in the reactor, and is a function of the volume of the reactor and the volumetric flow of the process ingredients through the reactor. A preferred residence time is about 15 sec to about 10 min, more preferably about 30 sec to about 5 min, especially preferably about 40 sec to about 2 min.

When the process fluids are being added to the reactor, it is preferred if they are preheated just before they enter the reaction to a temperature somewhat less than that of the actual reactor temperature, about 20° C. to about 150° C. less. This allows one to maintain a uniform constant temperature in the reactor itself, and for the newly added materials to start the polymerization reaction immediately upon entry to the reactor.

The amorphous polymers described herein are useful in a variety applications, many of which are related to the fact that the polymers are readily soluble in certain halogenated, especially perfluorinated solvents, and so the polymers are readily useable as films, coatings and encapsulants. Useful solvents include "dimer", perfluorobenzene, perfluoro(n-butyltetrahydrofuran), perfluorobenzene, perfluorotributylamine, and perfluoromorpholine.

Since the polymers are relatively chemically resistant, they may be used to encapsulate articles which must be protected from contamination, corrosion and/or unwanted adhesion to other materials. Films and coatings may be particularly useful because of the inherent properties of the polymer, such as, lack of crystallinity (polymer is clear), low surface energy (and hence poor wetting by water or most organic liquids), low dielectric constant, low index of refraction, low coefficient of friction, low adhesion to other materials, etc.

The TFE/HFP copolymers (including di- and terpolymers) of this invention can be used in many ways. One use is as a processing aid in polyolefins. This aspect of the invention is discussed in detail below.

The TFE/HFP and TFE/HFP/(III) copolymer solutions and copolymer/solvent systems of this invention can be used in many ways, making it possible to achieve end results that could not be achieved with previously available perfluoropolymers or could be achieved only in less convenient ways. These results include any of the results for which polymer solutions are used, such as coating, encapsulation, impregnation, and the casting of film. The copolymer solutions and copolymer/solvent systems of the invention can be employed in any of the methods by which solutions are known to be used, including dipping, painting, and spraying.

The copolymer solutions and copolymer/solvent systems of this invention can be used to make coatings on a broad range of substrate materials, including metal, semiconductor, glass, carbon or graphite, and natural and synthetic polymers. The substrates can be in a broad range of physical forms, including film or paper, foil, sheet, slab, coupon, wafer, wire, fiber, filament, cylinder, sphere, and other geometrical shapes, as well as in a virtually unlimited number of irregular shapes. Coatings can be applied by methods known in the art, including dipping, spraying, and painting. For plane substrates of suitable dimensions, spin coating can be employed. Porous substrates can also be coated or impregnated. These include, for example, screens, foams, microporous membranes, and woven and non-woven fabrics. In making such coatings, the solvent can be driven off by heat leaving a dry copolymer coating. Another advantage is that extremely thin coatings can be achieved, as thin as 100 angstroms or possibly even thinner depending on the coating characteristics required.

Coatings of the copolymers of this invention can be a sole coating on a substrate, or a component of a multilayer coating. For example, a TFE/HFP copolymer coating of this invention can be used as a first or primer, intermediate, or final coating in a multilayer fluoropolymer coating system. The coatings of this invention include coatings resulting from several successive applications of solution or copolymer/solvent systems to increase coating thickness to desired levels.

Coatings of this invention can consist of the copolymers of this invention alone, or of the copolymers admixed with minor amounts of other materials either soluble in the solvent or dispersed in the coating solution, suspension, or copolymer/solvent system. A minor amount can be up to about 10 wt % based on the combined weight of copolymer and additive.

Specific coated articles are within the scope of this invention.

Coated articles include polymer extrusion dies and molds for rubber and plastic parts, such as o-rings, bottle caps, golf balls, golf ball covers, golf ball cover half shells, and the like. The copolymers of this invention can be used in coatings. Both interior and exterior surfaces of extrusion dies may be coated to, respectively, facilitate extrusion and alleviate die drip buildup.

Coated articles include gasoline engine carburetor parts; internal parts of internal combustion engines such as valves and piston skirts; razor blades; metal containers such as cans, pans, trays, vessels, and the like; metal sheets and foils; continuous metal belts, metal rods, tubes, bars, profiles, and the like; bolts, nuts, screws, and other fasteners.

Coated articles include an article bearing a machine-readable marking on at least one surface, especially but not limited to a tag that can be attached to another object to provide information about inventory identification, contents, ownership, hazards, operating conditions, or maintenance requirements, for example.

Coated articles include wire for electrical and mechanical service. In either case, the metal wire may be solid or stranded. Wires for mechanical service include catheter guide wire and the actuating wire of push-pull cable.

Coated articles include rubber o-rings, seals, beading, gasketing, fish hooks, and the like.

Coated articles include paper and textile materials, including woven fabric including glass fabric, non-woven fabric, felts, and the like, fibers including filaments, yarns, e.g., staple and continuous filament, and strands.

Coated articles include foams, membranes, and the like.

Coated articles include optical fibers in which the substrate is a glass or plastic fiber.

Coated articles include semiconductors, semiconductor devices, magnetic storage media including disks, photoconductors, electronic assemblies, and the like, wherein the coating thickness may be as little as 200 angstroms or even as little as 100 angstroms or even as little as 50 angstroms. Use of solutions containing low concentrations of the TFE/HFP copolymer of this invention, e.g., as low as 0.001 wt % copolymer can be especially advantageous to form these very thin coatings.

One use for the TFE/HFP copolymers of this invention is as a processing aid in polyolefins. When the TFE/HFP copolymer of this invention is used as a processing aid in the polyolefin for film applications, the polyolefin generally will have a melt index (ASTM D-1238) of 5.0 or less at 190° C., preferably 2.0 or less. For high-shear melt processing such as fiber extrusion or injection molding, even high-melt-index resins, for example, those having a melt index of 20 or more, may suffer processing difficulties. Such polyolefins may comprise any thermoplastic hydrocarbon polymer obtained by the homopolymerization or copolymerization of one or more monoolefins of the formula $CH_2=CHR'$ wherein R' is an alkyl radical, usually of not more than eight carbon atoms. In particular, this invention is applicable to the following: polyethylene, both of the high-density type and the low-density type having densities within the range 0.89–0.97; polypropylene; polybutene-1; poly(3-methylbutene); poly(4-methylpentene); and linear low density copolymers of ethylene and an alpha-olefin, such as propylene, butene-1, pentene-1, hexene-1, heptene-1, octene-1, decene-1, octadecene-1, or n-methylpentene-1.

Because of the different melt characteristics of the olefin polymers mentioned, the addition of the fluoropolymer process aids of this invention may be of greater value in some polyolefins than in others. Thus, polyolefins such as polypropylene and branched polyethylene, that have low molecular weight or broad molecular weight distributions and, therefore, have good melt flow characteristics even at low temperature, may not require the use of the fluoropolymer additives or be noticeably improved by them, except under unusual, adverse extrusion conditions. However, for polymers such as high molecular weight, high density polyethylene or linear low density ethylene copolymers, particularly those with narrow or very narrow molecular weight distributions, addition of the fluoropolymers is especially beneficial.

Such polyolefins are typically processed by extrusion techniques at melt processing temperatures $T_p$ in the range of 175°–275° C. The commercially important blown-film process is usually carried out at $T_p$ in the range of 200°–250° C., and commonly at 200°–230° C.

The polyolefins and thus the polymer blend composition containing the fluoropolymer processing aid may contain assorted additives used in the art, such as but not limited to antioxidants, acid scavengers, light stabilizers, pigments, slip agents, and lubricants. In particular, finely divided solids such as silica or talc may be incorporated as antiblock agents.

The concentration of fluoropolymer processing aid in the host resin at fabrication into the final article should be high enough to achieve the desired effect in improving processibility, but not so high as to have adverse economic impact. The amount required can vary with the effect desired, the host resin, additives used in the host resin, and the processing conditions which may be different from the laboratory conditions reported in the following examples. Under certain conditions, concentrations of 100 ppm or less, as low as 50 ppm or even 25 ppm, can be effective. Under other conditions, the effective amount may be 1000, 2000, or even 5000 ppm. For special purposes, concentrations of 10% or even 25% may be appropriate. Thus from about 25 ppm to about 25% by weight of the fluoropolymer may be present, with preferred ranges being from about 100 ppm to about 10% by weight, and even more preferable, about 100 ppm to about 2000 ppm by weight of the fluoropolymer. The fluoropolymer processing aid can be incorporated into the host resin at the desired final concentration, or can be incorporated into a masterbatch or concentrate that is added to the host resin in a ratio calculated to yield the desired final concentration.

In the Examples, the $^{19}F$ NMR, which is used to determine the HFP distribution in the polymer, was measured on Bruker AC 250 NMR operating at 235 MHz. Polymer samples were loaded in 5 mm NMR tubes and heated to 250° to 360° C. in a narrow bore probe. In the melt, the methine CF's of the HFP units appear at −183.5 ppm if present as isolated units, at −179.5 if present as head to tail diads, and at −177 ppm if present as head to tail triads. It is uncertain whether or not the integration for the HFP triads at −177 ppm also includes higher (than triads) oligomeric blocks. The amount of HFP triads was determined from the ratio of the areas of the $^{19}F$ NMR signal at −177 ppm to the total areas of the signals at −177, −179.5 and −183.5 ppm.

Melt index tests were run using a Slocomb Model F extrusion plastometer with a 316 stainless steel die 0.947 cm in diameter and with a hole 0.318 cm long and 0.0794 cm in diameter. The plastometer was heated to 200° C. After loading 2 g samples of polymer, reinserting the piston, and waiting for 5 min for thermal equilibration, the piston was loaded with a weight so that the piston and dead weight together total 5 or 15 kg, as appropriate for the viscosity of the sample. The time required for all or part of the polymer to be extruded was measured, stopping after 5 min if the polymer showed no extrusion at all. The weight of polymer extruded divided by the number of minutes over which the extrusion occurred is reported here as the melt index. TGA measurements were done under nitrogen with a heating rate of 10° C./min.

In the Examples, the following abbreviations are used:
8CNVE—perfluoro(8-cyano-5-methyl-3,6-dioxa-1-octene)
Conv.—conversion
GPC—gel permeation chromatography
I.D.—inside diameter
Mn—number average molecular weight
Mw—weight average molecular weight
O.D.—outer diameter
PMVE—perfluoro(methyl vinyl ether)
In the Examples, the following materials are used:
"dimer"—a perfluorinated solvent which is defined in U.S. Pat. No. 5,237,049
FC-40—perfluorotributylamine
FC-75—perfluoro(n-butyltetrahydrofuran)
Kalrez® Perfluoroelastomer Parts—a tetrafluoroethylene/perfluoro(methyl vinyl ether) and curesite monomer copolymer part available from E. I. du Pont de Nemours and Company, Wilmington, Del., USA
Kapton® Polyimide Film—a polyimide film available from E. I. du Pont de Nemours and Company, Wilmington, Del., USA
Mylar® Polyester Film—a poly(ethylene terephthalate) film available from E. I. du Pont de Nemours and Company, Wilmington, Del., USA Nordel® Hydrocarbon Rubber—an EPDM elastomer available from E. I. du Pont de Nemours and Company, Wilmington, Del., USA PET—poly(ethylene terephthalate)

Viton® Fluoroelastomer—a copolymer of vinylidene fluoride and hexafluoropropylene available from E. I. du Pont de Nemours and Company, Wilmington, Del., USA

BRIEF DESCRIPTION OF THE DRAWING

In FIG. 1, within the barricade $NF_3$, initiator is loaded into loop (1) and then blown to reservoir (2) using hexafluoropropylene (HFP). In (2) tetrafluoroethylene is added to the HFP/$NF_3$ mixture, and the total mixture in (2) is then removed from the bottom of (2), boosted to a higher pressure and recirculated through the Monomer Recycle Loop, and then part of it is sent to the heated (polymerization) reactor (5) and part of it is recycled through valve (4) back to (2) after the pressure is lowered at pressure regulator (3) to the pressure of the contents of (2). After exiting reactor (5), the pressure of the mixture is reduced (often to atmospheric pressure) at back pressure regulator (6) and the copolymer product is isolated in glass collection bottle (7). Gaseous matter leaving the collection bottle is passed through meter (8) which is used to measure the amount of unreacted gaseous monomers. A more detailed description of the use of the apparatus of FIG. 1 appears below.

EXAMPLE 1

Continuous Polymerization in 10 ml Autoclave with Agitation

All the reactants needed for a single run were premixed in a reservoir, pressured to 103 MPa, bled off through a heated pressure vessel at slightly lower pressure, and finally vented to atmospheric pressure in the form of solid polymer foamed with unreacted monomer. The detailed procedure given below for Example 1 is in reference to the reactor schematic, FIG. 1.

Preparation of Homogeneous Monomer/Initiator Mix

Figure 1:
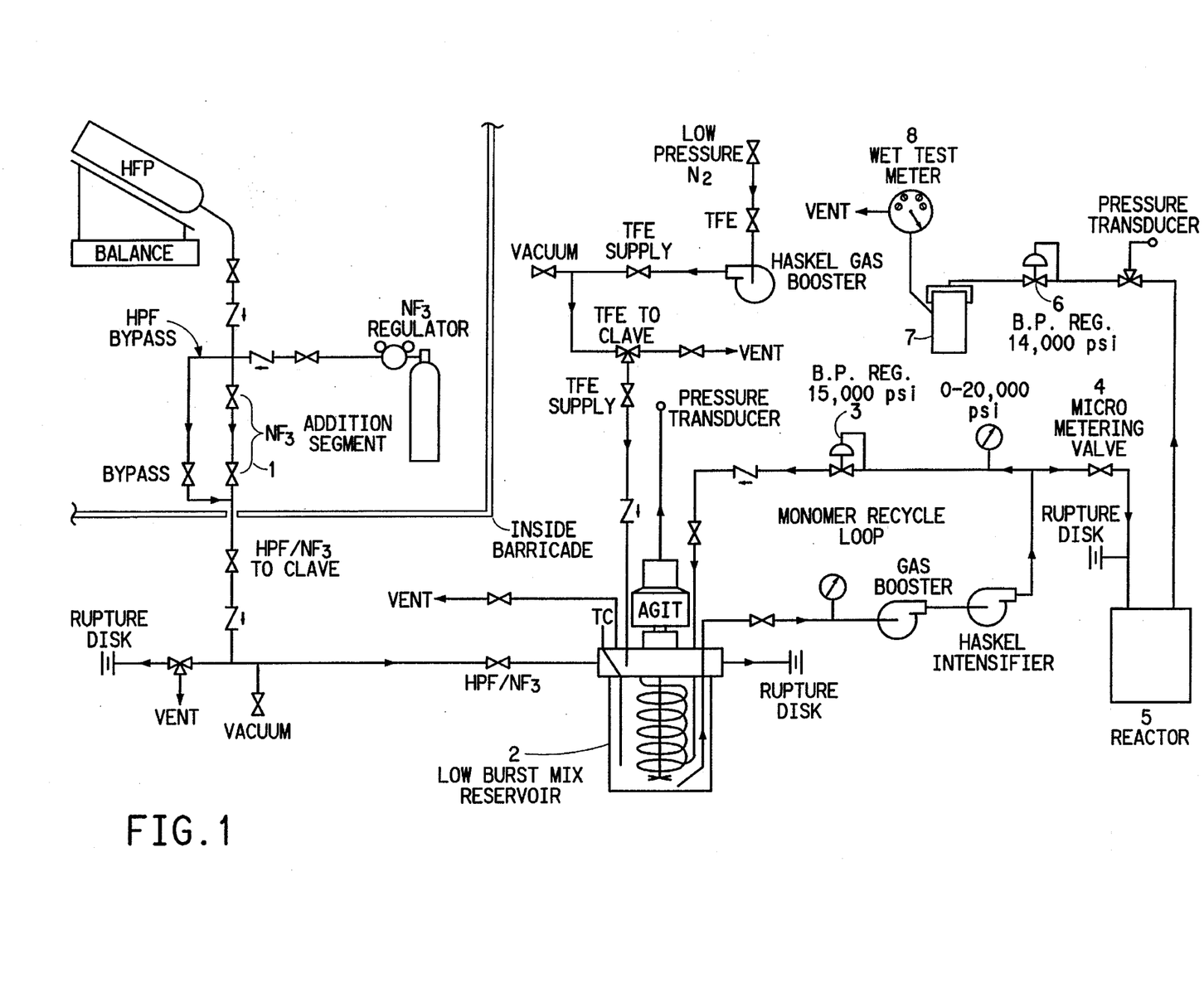
FIG. 1 is a schematic diagram of a High Pressure Continuous Unit which can be used for the continuous polymerization described herein.

A 25 ml loop (1) off the feed line to a 3.8 L reservoir (2) was pressured to 710 kPa with nitrogen trifluoride at ambient temperature (~0.6 g of $NF_3$). The 3.8 L reservoir was then loaded with 160 g of TFE and 4000 g of HFP, a portion of the HFP being used to blow the $NF_3$ into the reservoir (2). Liquid monomer phase was pulled off the bottom of the reservoir, pressured to 103 MPa, and then recirculated back to the reservoir via back pressure regulator (3). The run was not started until the contents of the clave had been mixed by 10 minutes of such recirculation. Recirculation through the reservoir was maintained for the duration of the run. No effort was made to control the temperature of the reservoir which varied in the case of this run from 23° C. at the start to 33° C. at the finish.

Monomer Feed to Reactor

Flow was maintained through the system by letting monomer pressure down in stages, from 103 MPa in the recirculation loop to 96.5 MPa in the reactor and finally to atmospheric pressure in the product collector. The rate of flow was controlled by a micrometering valve (4) in the stainless steel line that connected the reservoir recirculation loop at 103 MPa with the reactor at 96.5 MPa. Reactor pressure was maintained at 96.5 MPa by back pressure regulator (6) placed after reactor (5). Micrometering valve (4) was opened until monomer flowed through the reactor at 10 to 12 g per minute, the measurement of flow rates being discussed later. In order to maintain steady flow throughout the run, periodic adjustments were made to micrometering valve (4).

Reactor

As already mentioned, a flexible stainless steel tube, 0.40 cm O.D. by 0.16 cm I.D., was run from micrometering valve (4) to the front end of reactor (5). In an effort to bring the monomers up to reactor temperature rapidly, the last ~61 cm of tubing before the reactor was wrapped with electrical tape and preheated to ~200° C. Considering that the internal volume of this preheated segment is small relative to the reactor proper (~1 ml in the preheated line vs. 10 ml in the reactor) and that reaction rates are slower at 200° C. than at 275° C., polymer formation in the preheated line was ignored for the purposes of productivity calculations. Reactor (5), in this Example a 10 cc stainless steel autoclave (5.2 cm long X 1.1 cm I.D. and containing two loose 0.63 cm stainless steel balls), was rocked vigorously with a paint shaker while heating to 275° C.

Product Isolation

A piece of flexible stainless steel tubing was run from reactor (5) to back pressure regulator (6) at which point pressure was dropped from 96.5 MPa to atmospheric. In spite of the fact that no effort was made to warm either the line or the valve, no plugging was observed in this and the majority runs. When plugging did occur, it was most often at the low pressure side of the regulator (6) where foamed polymer was left when the monomer flashed off. To minimize plugging, the low pressure side of the let down valve was drilled out to provide as large an orifice as possible and then connected directly to a several liter glass collection bottle (7). Gaseous monomer exiting the glass collection bottle was passed through wet test meter (8), the liters of monomer per minute being converted to monomer flow in grams per minute. An average flow rate of 10.9 g/min was thus observed over the 247 minute duration of this run. Given that the density of HFP at 275° C./96.5 MPa is ~1.29 g/ml, the average residence time for the monomers in reactor (5) was ~1.2 minutes. Polymer was recovered from the glass collection bottle (7) as large chunks of foamed white solid weighing 170.2 g. Pulling residual monomer off with a vacuum pump reduced the weight of polymer to 159 g for a productivity of 3.8 kg/L/hr. Fluorine NMR of the polymer melt at 330° C. found 43 mole % (53 wt %) HFP copolymerized with 57 mole % (47 wt %) TFE, allowing the calculation of 72% TFE conversion per pass and 3.2% HFP conversion per pass. Rolling 1.5 g of this polymer with 5 ml of FC-75 at room temperature gave a viscous solution. Transparent films were pressed at 160° C. by applying 8000 lbs of pressure for 1 minute to 1 g samples held between Kapton® polyimide film cover sheets. Under an applied weight of 15 kg, a 2 g sample extruded through a melt indexer at 0.63 g/minute at 200° C. GPC in FC-75 solvent showed Mw=235,000 and Mn=94,700 for a Mw/Mn=2.87.

Characterization Summary

The results of Example 1 as well as of Examples 2 to 13 made under the same conditions are tabulated below. Reproducibility was excellent considering that the process has yet to be automated.

| Ex. | Residence Time | Polymer Wt % HFP[1] | Melt Index[2] | Conv. Per Pass HFP | Conv. Per Pass TFE | kg/L/hr | Mw/Mn[3] | $N_{inh}$[4] |
|---|---|---|---|---|---|---|---|---|
| 1 | 1.2 min | 53% | 0.6 g/min | 3.2% | 72% | 3.8 | 2.87 | 0.39 |
| 2 | 0.9 min | 45% | 0.4 g/min | 2.3% | 72% | 4.2 | 3.65 | 0.45 |
| 3 | 1.0 min | 50% | 0.3 g/min | 2.6% | 65% | 3.9 | 3.53 | 0.54 |
| 4 | 0.9 min | 49% | 0.5 g/min | 2.3% | 59% | 3.7 | 3.63 | 0.49 |
| 5 | 1.0 min | 51% | 0.4 g/min | 2.5% | 61% | 3.8 | 3.23 | 0.49 |
| 6 | 1.0 min | 51% | 0.6 g/min | 2.7% | 65% | 3.9 | 3.34 | 0.51 |
| 7 | 1.0 min | 51% | 1.3 g/min | 2.6% | 63% | 3.8 | 3.12 | 0.41 |
| 8 | 1.0 min | 50% | 0.7 g/min | 2.5% | 63% | 3.6 | 2.99 | 0.44 |
| 9 | 1.0 min | 54% | 1.0 g/min | 2.7% | 58% | 3.6 | 3.83 | 0.29 |
| 10 | 1.1 min | 53% | 0.7 g/min | 3.2% | 70% | 3.8 | 2.85 | 0.41 |
| 11 | 1.2 min | 50% | 0.8 g/min | 3.0% | 76% | 3.7 | 2.62 | 0.39 |
| 12 | 1.1 min | 53% | 0.7 g/min | 2.8% | 63% | 3.5 | 2.45 | 0.48 |
| 13 | 1.2 min | 53% | 1.0 g/min | 3.2% | 70% | 3.6 | 2.57 | 0.41 |

[1]Composition determined by fluorine NMR in the melt at 300–340° C.
[2]Melt index, determined at 200° C. with a 15 kg weight
[3]Mw and Mn determined by GPC using FC-75 solutions, versus linear poly(hexafluoropropylene oxide) standards, one with Mn ~20,000, the other with Mn ~70,000
[4]Inherent viscosity in FC-75

COMPARATIVE EXAMPLE 1

An 85 ml autoclave was loaded with 60 ml of perfluorodimethylcyclobutane and 0.25 g of cobalt trifluoride. The autoclave was sealed, chilled, and evacuated. Hexafluoropropylene was used to sweep in 4.25 g of TFE. Enough HFP was added to bring the pressure of the autoclave to 930 MPa at 23° C. (~30 g of HFP). The autoclave was heated to 199° C. and 296 MPa, an additional 6.9 MPa of HFP being added to match Eleuterio's condition of 303 MPa. The autoclave was held at ~200° C. for four hours and then cooled and vented. The resulting polymer solution was filtered to get rid of pink residues (presumably containing insoluble cobalt compounds), stripped to heavy oil on a rotary evaporator and then blown down to 0.94 g of solid using a stream of nitrogen. This solid has an inherent viscosity of 0.207 in FC-75 closely matching Eleuterio's Example II. Mw/Mn was 6.39, a very broad molecular weight distribution compared to polymers made by our process. In a TGA analysis, this polymer had lost 20% of its weight by 340° C.

| Ex. | Residence Time | Polymer Wt % HFP | Melt Index | Conv. Per Pass HFP | Conv. Per Pass TFE | kg/L/hr | Mw/Mn |
|---|---|---|---|---|---|---|---|
| Com. 1 | 240 min | 57% | — | — | — | 0.02 | 6.39 |

EXAMPLES 14 TO 19

Continuous Polymerization in 10 mL Autoclave, With and Without Agitation

The same set up was used as in Examples 1 to 13. Half as much monomer was loaded, the initiator relative to monomer was twice as great as in Examples 1 to 13, and reactor temperature was 300° to 325° C. instead of 275° C. In all Examples but 14 the reactor was agitated by vigorous rocking. Product characterizations are shown below.

| Ex. | Residence Time | Polymer Wt % HFP[1] | Melt Index[2] | Conv. Per Pass HFP | Conv. Per Pass TFE | kg/L/hr | Mw/Mn[3] |
|---|---|---|---|---|---|---|---|
| NO SHAKING, 300° C. | | | | | | | |
| 4 | 0.9 min. | 51% | 2 g/min | 2.7% | 64% | 3.9 | 3.57 |
| SHAKING, 300° C. | | | | | | | |
| 15 | 0.5 min. | 46% | 20 g/min | 1.2% | 36% | 4.0 | 2.79 |
| 16 | 0.7 min. | 56% | 2 g/min | 2.7% | 52% | 4.4 | 2.12 |
| 17 | 0.9 min. | 55% | 20 g/min | 4.1% | 84% | 5.5 | 3.60 |
| 18 | 1.9 min. | 60% | 20 g/min | 5.4% | 91% | 3.2 | 2.41 |
| SHAKING, 325° C. | | | | | | | |
| 19 | 0.9 min. | 60% | 4 g/min | 5.3% | 86% | 6.4 | 2.38 |

[1]Composition determined by fluorine NMR in the melt at 300–340° C.
[2]Ex. #14 melt index at 200° C. with 15 kg weight
Ex. #15 melt index at 200° C. with 15 kg weight
Ex. #16 melt index at 200° C. with 15 kg weight
Ex. #17 melt index at 200° C. with 15 kg weight
Ex. #18 melt index at 200° C. with 15 kg weight
Ex. #19 melt index at 200° C. with 5 kg weight
[3]Mw and Mn determined by GPC using FC-75 solutions, versus linear poly(hexafluoropropylene oxide) standards, one with Mn ~20,000, the other with Mn ~70,000

EXAMPLES 20 TO 44

Continuous Polymerization in Tube, No Agitation

The same set up was used as for Examples 1 to 13, except that in these Examples reactor (5) was a 0.95 cm OD x 0.52 cm ID x 5.3 m long coil of stainless steel tubing with an internal volume of ~110 ml. The reactor coil was heated using a sand bath. In view of the 5.3 m length of the tube no preheater was needed. Results for Examples 20 to 44 are shown in the table below. Example 43 was unique in that 435 ml of liquid FC-75 was added along with the initial monomer charge. The result of doing this is that the product was obtained as ~400 ml of solution containing 0.16 g of dissolved polymer/ml.

|     |        |      |          | Weight % HFP |          | % Conversion |      |         |
| --- | ------ | ---- | -------- | ------------ | -------- | ------------ | ---- | ------- |
| Ex. | °C.    | MPa  | Res Time | Feed         | Polymer[1] | HFP        | TFE  | kg/L/hr |
| ~CONSTANT T, P, AND FEED | | | | | | | | |
| 20  | 250° C. | 75.8 | 21 min. | 98% | 64% | 2.9 | 81 | 0.2 |
| 21  | 250° C. | 75.8 | 9 min.  | 98% | 61% | 2.2 | 72 | 0.3 |
| 22  | 250° C. | 75.8 | 5 min.  | 98% | 59% | 2.2 | 76 | 0.5 |
| 23  | 250° C. | 75.8 | 4 min.  | 98% | 58% | 1.5 | 55 | 0.7 |
| 24  | 250° C. | 75.8 | 3 min.  | 98% | 58% | 1.3 | 37 | 0.6 |
| CONSTANT T, P, AND ~TIME | | | | | | | | |
| 25  | 250° C. | 96.5 | 6 min. | 98% | 58% | 2.3 | 84 | 0.6 |
| 26  | 250° C. | 96.5 | 6 min. | 96% | 53% | 3.8 | 84 | 0.9 |
| 27  | 250° C. | 96.5 | 6 min. | 96% | 54% | 3A  | 72 | 0.9 |
| 28  | 250° C. | 96.5 | 6 min. | 96% | 52% | 3.2 | 74 | 0.9 |
| 29  | 250° C. | 96.5 | 6 min. | 96% | 53% | 3.8 | 86 | 1.0 |
| 30  | 250° C. | 96.5 | 6 min. | 95% | 50% | 4.3 | 80 | 1.1 |
| 31  | 250° C. | 96.5 | 6 min. | 94% | 44% | 2.9 | 56 | 0.8[2] |
| 32  | 250° C. | 96.5 | 8 min. | 92% | 47% | 4.6 | 63 | 0.9[2] |
| CONSTANT P, FEED, AND ~TIME | | | | | | | | |
| 33  | 275° C. | 75.8 | 18 min. | 98% | 67% | 3.3 | 85 | 0.2 |
| 34  | 250° C. | 75.8 | 21 min. | 98% | 64% | 2.9 | 81 | 0.2 |
| 35  | 225° C. | 75.8 | 21 min. | 98% | 57% | 1.7 | 65 | 0.1 |
| 36  | 325° C. | 96.5 | 6 min.  | 96% | 59% | 5.1 | 89 | 1.1 |
| 37  | 300° C. | 96.5 | 5 min.  | 96% | 56% | 5.4 | ~100 | 1.4 |
| 38  | 275° C. | 96.5 | 7 min.  | 96% | 59% | 5.2 | 90 | 1.0 |
| 39  | 250° C. | 96.5 | 6 min.  | 96% | 53% | 3.8 | 84 | 0.9 |
| CONSTANT T, FEED, AND ~TIME | | | | | | | | |
| 40  | 250° C. | 62.0 | 5 min. | 98% | 59% | 1.9 | 65 | 0.5 |
| 41  | 250° C. | 75.8 | 5 min. | 98% | 59% | 2.2 | 76 | 0.5 |
| 42  | 250° C. | 96.5 | 6 min. | 98% | 60% | 2.3 | 75 | 0.6 |
| IN THE PRESENCE OF FC-75 SOLVENT AND THIRD MONOMER, 8CNVE | | | | | | | | |
| 43  | 250° C. | 96.5 | ~6 min. | 90+%[3] | 64%[3] | 2.3 | 31 | 0.4 |
| IN THE PRESENCE OF THIRD MONOMER, PMVE | | | | | | | | |
| 44  | 250° C. | 96.5 | ~6 min. | 94%[4] | 47%[4] | 3.1 | ~100 | 0.9 |

[1]Composition determined by fluorine NMR in the melt at 300–340° C.
[2]Incomplete removal of polymer from reactor, kg/L/hr probably larger than reported
[3]Several percent 8CNVE, $CF_2=CFOCF_2CF(CF_3)OCF_2CF_2CN$ in feed. Polymer composition by fluorine NMR: 63.8 wt % HFP, 34.1 wt % TFE, 2.1 wt % 8CNVE
[4]Starting mix: 94.3% wt % HFP, 3.8 wt % TFE, 1.9 wt % PMVE Polymer: 37.2 mole% HFP, 60.7 mole % TFE, 2.1 mole % PMVE Molecular weight distributions were measured for only a few of the samples made in the tubular reactor. Distributions appear to be a bit broader and less uniform than experienced in the autoclave.

| Example | Mw/Mn |
| --- | --- |
| 38 | 4.96 |
| 27 | 3.20 avg. of 2 |
| 28 | 3.93 avg. of 2 |
| 29 | 3.48 avg. of 2 |

EXAMPLES 45 TO 49

Continuous Polymerization in Tube, No Agitation
Effect of Decreasing Initiator

The same tubular reactor as described in Examples 20 to 44 was run at 250° C./96.5 MPa with a residence time of 5.6 to 6.0 minutes and 2500 g HFP+50 g TFE+a variable amount of $NF_3$ added to the 3.8 L mixing reservoir. The effects of varying the amount of $NF_3$ in the starting monomer mix is shown below.

|     | Estimated Grams | Wt % BFP | | % Conversion | | |
| --- | --- | --- | --- | --- | --- | --- |
| Ex. | $NF_3$ in Feed[1] | Feed | Polymer | HFP | TFE | Kg/L/hr |
| 45  | 0.7 g | 98% | 58% | 2.3 | 84 | 0.6 |
| 46  | 0.4 g | 98% | 58% | 1.6 | 56 | 0.4 |
| 47  | 0.2 g | 98% | 60% | 1.8 | 62 | 0.4 |
| 48  | 0.1 g | 98% | 58% | 1.5 | 54 | 0.3 |
| 49  | None  | 98% | 57% | 0.7 | 28 | 0.2 |

[1]The grams of $NF_3$ added to the monomer mixing reservoir were estimated from PV = nRT. The amount of $NF_3$ delivered to the reactor for polymerization, however, may be quite a bit less if the highly volatile $NF_3$ concentrates in the vapor phase rather than in the liquid monomer phase that is pumped to the reactor.

Initiation in the absence of $NF_3$ is probably the result of adventitious oxygen. Shown immediately below are the results of 19F NMR analyses giving the percentages of HFP repeat units which are isolated, in diads and in triads for certain Examples.

| Example # | Wt. % HFP | % of Total CF's Found in | | | $^{19}$F NMR |
|---|---|---|---|---|---|
| | | Triads | Diads | | Isolated |
| 34 | 67% | 12.40 | 41.47 | | 46.13 |
| 35 | 64% | 15.86 | 39.42 | | 44.72 |
| 23 | 59% | 9.06 | 36.72 | | 54.22 |
| 36 | 57% | 9.92 | 35.59 | | 54.49 |
| 33 | 47% | 5.56 | 25.53 | | 68.91 |
| Comparative Example #1 | 57% | 26.63 | 27.26 | | 46.4 |

EXAMPLE 50

The agitated reactor was set up as in Example 1. Instead, however, of using $NF_3$ as the initiator, a solution of 0.8 ml of perfluorodibutylamine [$(C_4F_9)_2NF$] dissolved in 5 ml of HFP cyclic dimer (perfluorodimethylcyclobutane) was introduced directly in the 1 gallon reservoir 2 prior to the start of the run. A mix of this initiator with 160 g of TFE and 4000 g of HFP was run through the 10 ml agitated reactor at ~12 g/min at 275° C. (estimated residence time 1 minute) and 96.5 MPa for 315 minutes. This gave 146 g of poly-(HFP/TFE), for a productivity of 28 kg/L/hr. The polymer was soluble in FC-75 and found to have Mw=603,000, Mn=226,000, and Mv=546,000. Fluorine NMR in the melt at 340° C. found 49 wt % HFP, 51 wt % TFE, and 74.% of the methine FC's as triads. Conversion per pass was 50% for TFE and 1.9% for HFP.

EXAMPLES 51–55

The agitated reactor was set up as in Example 1. Instead, however, of using $NF_3$ as the initiator, a solution of 1.5 g of perfluorodibutylamine [$(C_4F_9)_2NF$] dissolved in 5 ml of HFP cyclic dimer (perfluorodimethylcyclobutane) was introduced directly in the 1 gallon reservoir 2 prior to the start of the run. A mix of the initiator with 160 g of TFE and 4000 g of HFP was run through the 10 ml agitated reactor at 9.5 g/min at 325° C. (estimated residence time 1.2 min) and 96.5 MPa for 365 minutes. This gave 239 g of poly-(HFP/TFE), for a productivity of 40 kg/L/hr. The polymer was soluble in FC-75. Fluorine NMR in the melt at 320° C. found 54 wt % HFP/46 wt % TFE with 6.1% of the HFP methines as triads. GPC in FC-75 found Mw=348,000, Mn=130,000, Mv=304,000. Inherent viscosity in FC-75 was 0.413. Per pass conversions were 82% for TFE and 3.9% for HFP.

A major difference between $NF_3$ and $(C_4F_9)_2NF$ is that $(C_4F_9)_2NF$ is a relatively nonvolatile liquid. This means that when a mix of HFP, TFE, and $(C_4F_9)_2NF$ is made in mixing reservoir 2, almost all of the $(C_4F_9)_2NF$ will reside in the liquid monomer phase. This in turn allows us to estimate with moderate accuracy how much $(C_4F_9)_2NF$ was actually used as an initiator in this run: when 3472 g out of 4160 g (83%) of starting monomer mix was pumped through reactor 5, a like fraction of the $(C_4F_9)_2NF$, 83% or ~1.24 g, was probably used to initiate polymerization. Knowing that 1.24 g of $(C_4F_9)_2NF$ initiated 239 g of polymer with Mn=130,000 and assuming that there are two $(C_4F_9)_2NF$ derived end groups per chain allows one to calculate that each $(C_4F_9)_2NF$ generated in fact 1.4 radicals. Generating 1.4 radicals out of a potential maximum of 2 [F• and $(C_4F_9)_2N$•] represents an initiator efficiency of 70% for $(C_4F_9)_2NF$ at 325° C. A similar calculation for Example 50 above shows that the efficiency of $(C_4F_9)_2NF$ drops to about 26% at 275° C.

Properties of the $(C_4F_9)_2NF$ initiated polymer made here in Example 51 are compared to those of closely bracketing $NF_3$ initiated runs (Examples 52 to 55) made in the same equipment:

| Ex. # | Gel Permeation Chromatography Data | | | | | $^{19}$F NMR DATA | |
|---|---|---|---|---|---|---|---|
| | Mw × $10^{-3}$ | Mn × $10^{-3}$ | Mw/Mn | Mv × $10^{-3}$ | IV | Wt % HFP | Triads |
| 52 | 334 | 129 | 2.59 | 292 | 0.411 | 53% HFP | 6.5% |
| 51 | 348 | 130 | 2.67 | 304 | 0.413 | 54% BFP | 6.1% |
| 53 | 371 | 142 | 2.99 | 326 | 0.443 | 50% HFP | 5.3% |
| 54 | 423 | 137 | 3.08 | 367 | 0.492 | 51% BFP | 5.0% |
| 55 | 451 | 156 | 2.90 | 397 | 0.517 | 48% BFP | 3.2% |

EXAMPLE 56

The agitated reactor was set up as in Example 1. Instead, however, of using $NF_3$ as the initiator, 11 psig of $CF_3OOCF_3$ (about 0.3 g) was introduced into a 25 ml initiator loop 1. A mix of this initiator with 160 g of TFE and 4000 g of HFP was run through the 10 ml agitated reactor at about 10.6 g/min at 275° C. and 14,000 psi for 340 minutes. This gave 53 g of poly(HFP/TFE), for a productivity of 13.3 kg/L/hr. The polymer was soluble in FC-75 and found to have Mw=852,000 and Mn=235,000.

EXAMPLE 57

A 50 wt % HFP copolymer of HFP and TFE, which had a melt viscosity of 100 sec$^{-1}$ of 854 Pa.s was dissolved in a variety of solvents to test solubility. To an Erlenmeyer flask fitted with a reflux condenser and magnetic stirrer were added 95 g various solvents and 5 g polymer. The mixtures were heated on a hot plate with stirring until reflux occurred. The solvents tested were "dimer", FC-75, FC-40 and hexafluorobenzene.

The polymer dissolved in all solvents tested to form clear, low viscosity solutions. When cooled to room temperature, all samples remained as clear, low viscosity fluids.

EXAMPLE 58

The FC-75 solution of Example 57 was used to prepare dipped coatings on various metals. Metal coupons of size 2.5 cm x 7.6 cm x 0.64 mm were cleaned in an ultrasonic bath with acetone, dried at 150° C. for 4 hours, cooled to room temperature and dipped into the 5% solution. Excess solution was drained off. The coupons were dried overnight at 150° C. Metals tested were copper, brass, aluminum, stainless steel, galvanized steel and chrome plated steel. All coatings were smooth and clear. The copper coupon had some discoloration.

Contact angle measurements of a droplet of water on each coating were made. Contact angles were 115°+/–2° advancing and 94°+/–2° receding, showing that the coatings were uniform and were hydrophobic.

Film thickness was measured for each coupon using a Tencor Stylus Profilometer. Film thickness was 1.7 μm +/–0.5 μm.

Film adhesion was tested using ASTM D3359. Each coated film was scratched in a cross hatch pattern of 10 lines per 2.5 cm using a razor knife edge. Adhesive tape was pressed against the cross hatch scored film. The tape was removed and the film examined. No removal of polymer film from the metal coupon occurred. The cross hatched scored coated films were placed in boiling water for 1 hour. The coupons were removed from the water, dried at 150° C. for 1 hour and were cooled to room temperature. An adhesive tape was again pressed against the cross hatch scored film and then removed. No removal of polymer film from the metal coupon occurred. This shows that the coated films are strongly adhered to the metal coupons and can resist the action of boiling water.

EXAMPLE 59

The FC-75 solution of Example 57 was used to prepare dipped coatings on various polymers. Polymer strips of size 2.5 cm x 7.6 cm x 1.9 mm were prepared from nylon 6, 6, Nordel® vulcanizate, neoprene vulcanizate, Viton® vulcanizate, Kalrez® vulcanizate, and strips of size 2.5 cm. x 7.6 cm x 0.25 mm were cut from films of Mylar® PET and Kapton® polyimide. All samples were cleaned in an ultrasonic bath with acetone, dried at 150° C. for 4 hours, cooled to room temperature and dipped into the 5% solution. Excess solution was drained off. The coated samples were dried overnight at 150° C. All coatings were smooth and clear.

Contact angle measurements of a droplet of water on each coating were made. Contact angles were 115°+/–4° advancing and 94°+/–4° receding, showing that the coatings were uniform and were hydrophobic.

Film thickness was measured for coatings on nylon, Mylar® and Kapton® using a Tencor Stylus Profilometer. Film thickness was 1.7 µm+/–0.5 µm.

Film adhesion was tested using ASTM D3359. Each coated film was scratched in a cross hatch pattern of 10 lines per 2.5 cm using a razor knife edge. Adhesive tape was pressed against the cross hatch scored film. The tape was removed and the film examined. No removal of the coated film from the polymer surface occurred. The cross hatch scored coated strips were placed in boiling water for 1 hour. The strips were removed from the water, dried at 150° C. for 1 hour and were cooled to room temperature. An adhesive tape was again pressed against the cross hatch coating and then removed. No removal of coating film from the polymer strips occurred. This shows that the coated films are strongly adhered to the polymer strips and can resist the action of boiling water.

EXAMPLE 60

The solution of Example 57 in FC-75 was used to prepare dipped coatings on various fabrics. Pieces of fabric were cut to size 15.2 cm square. The fabrics were a loose woven nylon, a loose woven PET polyester, a loose woven cotton and a Nomex® felt. The fabrics were dipped into the 5% solution and were squeezed by hand to remove excess solution. The fabrics were dried for 1 hour at 150° C. After drying, all fabrics remained soft and flexible and were porous.

A drop of distilled water was placed on each fabric and on a portion of the same fabric that had not been treated. In each case, the water wet and penetrated the untreated fabric, but formed a spherical drop on the treated fabric and did not penetrate. Thus, the treated fabrics were hydrophobic.

EXAMPLE 61

The solution of Example 57 in FC-75 was treated as a mold release agent. A size 214 O-ring mold was cleaned with "Easy Off" commercial oven cleaning agent. The mold was washed with water and dried by heating in a press at 177° C. for 15 min. The mold had 30 sites for molding O-rings. Fifteen sites were spray coated with solution. The remaining sites were coated with commercial mold release, McLube No. 1725. The coatings were dried by placing the mold in a press at 177° C. for 15 min. Kalrez® O-ring preforms were placed in the proper sites and the mold was placed in a press at 177° C. for 15 min to mold the O-rings.

After the first molding cycle there was some sticking to the McLube coated sites. The solution coated sites had no sticking. The mold cycle was repeated for three additional cycles with no additional mold release coating applied to any of the sites. After the final mlding cycle, about 30% of the O-rings removed from the sites lubricated with McLube were torn during removal from the mold due to sticking. None of the O-rings removed from sites coated with solution were torn. There was no sticking of O-rings at the solution coated sites.

EXAMPLE 62

The solution of Example 57 in FC-75 was tested as a mold release agent. A conventional golf ball compression mold was cleaned with "Easy Off" commercial oven cleaning agent. The mold was washed with water and dried by heating in a press at 204° C. for 15 min. The mold was spray coated with solution and was dried by placing the mold in a press at 204° C. for 4 hours. The mold cavity was filled with a Surlyn® ionomer golf ball cover and a spiral wound rubber core. The golf ball was compression molded for 15 min at 204° C.

When the mold was used without solution coating, the golf ball cover adhered to the metal mold and pulled away from the core when the ball was removed from the mold. When the mold was coated with the solution there was no sticking and the molded golf ball was easily removed.

EXAMPLE 63

A linear low density polyethylene with melt index 1 g/10 min was extruded through a capillary die of size 0.76 mm x 2.5 cm x 90° using an Instron® capillary rheometer. The shear stress required to extrude the polyethylene at 220° C. at a shear rate of 347 sec$^{-1}$ was 4.0×10$^5$ Pa. The surface of the extrudate was rough and distorted.

To the polyethylene was added TFE/HFP copolymer at a level of 0.1%. The extrusion through the capillary die was repeated. When the polyethylene containing the TFE/HFP copolymer was extruded at 220° at a shear rate of 347 sec$^{-1}$ the shear stress required was reduced to 2.0×10$^5$ Pa, and the extrudate was smooth and was not distorted. Thus, the presence of the copolymer reduced the shear stress required to extrude the polyethylene from 4.0×10$^4$ Pa to 2.0×10$^4$ Pa and the surface of the extrudate became smooth and undistorted. The TFE/HFP copolymer acted as a processing aid for the polyethylene.

EXAMPLE 64

An 0.38 mm x 9.5 mm x 90° tungsten carbide capillary was coated with a 1% solution of TFE/HFP copolymer dissolved in FC-75. The coating was dried at 250° C. for 2 hours. A linear low density polyethylene, GRSN 7047 from Union Carbide, melt index 1 g/10 min, containing 2.5% colloidal silica (to act as an abrasive material) was extruded through the capillary die using an Instron capillary rheometer at a temperature of 220° C. and at a shear rate of 833 sec$^{-1}$.

When the polyethylene was extruded through the capillary die with no solution coating on the capillary, at a temperature of 220° C. and at a shear rate of 833 sec$^{-1}$ the shear stress required was 4.5×10$^5$ Pa. The surface of the extrudate was rough and distorted. When the polyethylene was extruded through the coated capillary under the same conditions, the shear stress required dropped to 2.5×10$^5$ Pa shortly after start up and the surface of the extrudate was smooth and undistorted. The shear stress slowly rose, over a period of about 2 hours to 4.5×10$^5$ Pa, as the solution coating was slowly worn away by the abrasive polyethylene. When the shear stress reached a level greater than 3.0×10$^5$ Pa the surface of the extrudate again became rough. This example shows that the solution coating on the capillary acted as an extrusion aid that significantly reduced shear stress and eliminated surface roughness. When the coating was completely worn away, after two hours, the shear stress returned to the uncoated value and surface roughness reappeared.

EXAMPLE 65

Polymerization in Presence of $CO_2$

The agitated reactor was set up as in Example 1, loading a mixture of 3000 g of HFP, 160 g of TFE, 157 g of $CO_2$ diluent, and 1.5 g of $NF_3$. This mixture was run through the 10 cc agitated reactor at about 10 to 11 g/min at 300° C. and 96.5 MPa for 278 minutes. This gave 254 g of polymer for a productivity of 46 lbs/gallon/hr. The polymer had an inherent viscosity of 0.254 and a melt flow of 4 g/min at 200° C. under a load of 5 kg in a melt indexer.

What is claimed is:

1. A continuous polymerization process, comprising, contacting at a pressure of about 41 MPa to about 690 MPa, and a temperature of about 200° C. to about 350° C., tetrafluoroethylene, hexafluoropropylene, and a radical initiator, to produce an amorphous polymer which contains at least 30 mole percent of repeat units derived from said hexafluoropropylene, at least 1 mole percent of repeat units derived from said tetrafluoroethylene, and provided that said continuous polymerization has an average residence time of about 1 second to about 10 minutes.

2. The process as recited in claim 1 wherein said pressure is about 55 MPa to 172 MPa.

3. The process as recited in claim 1 wherein said pressure is about 69 MPa to about 103 MPa.

4. The process as recited in claim 1 wherein said temperature is about 225° C. to about 325° C.

5. The process as recited in claim 1 wherein said radical initiator is $NF_3$, $R_fNF_2$, $(R_f)_2NF$, $R_fN=NR_f$, 5 or 6 member ring perfluorinated heterocycle containing at least one N—F group and optional $R_f$ groups, $R_fN=NR_f$, $R_fOOR_f$, perfluoropyrrolidine, perfluorooxazoline, perfluoropiperidine, perfluoromorpholine or perfluoropiperazine, wherein $R_f$ is perfluoroalkyl, containing 1 to 20 carbon atoms and having optional in-chain oxygen.

6. The process as recited in claim 5 wherein said radical initiator is $NF_3$, $(R_f)_2NF$, $R_fNF_2$, perfluoropyrrolidine, perfluoropiperidine, perfluoromorpholine, or perfluoropiperazine.

7. The process as recited in claim 1 wherein said average residence time is about 30 sec to about 5 min.

8. The process as recited in claim 1 wherein another monomer which is an α-perfluoroolefin, a perfluorocycloolefin or a perfluoro(alkyl vinyl ether) is also present.

9. The process as recited in claim 2 wherein said temperature is about 225° C. to about 325° C., said radical initiator is $NF_3$, and said average residence time is about 30 sec to about 5 min.

10. The process as recited in claim 1 wherein said initiator is $NF_3$.

11. The process of claim 1 carried on in an agitated reactor.

12. The process as recited in claim 1 wherein one or more other copolymerizable monomers are also present.

* * * * *